(12) United States Patent
San et al.

(10) Patent No.: US 8,236,525 B2
(45) Date of Patent: Aug. 7, 2012

(54) REDUCED PHOSPHOTRANSFERASE SYSTEM ACTIVITY IN BACTERIA

(75) Inventors: Ka-Yiu San, Houston, TX (US); George N. Bennett, Houston, TX (US); Thomas Bryce Causey, Ipswich, MA (US); Matthew Sing Wong, Houston, TX (US); Steven Wu, Houston, TX (US)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 12/596,399

(22) PCT Filed: Apr. 15, 2008

(86) PCT No.: PCT/US2008/060383
§ 371 (c)(1),
(2), (4) Date: Mar. 24, 2010

(87) PCT Pub. No.: WO2008/128234
PCT Pub. Date: Oct. 23, 2008

(65) Prior Publication Data
US 2010/0196958 A1   Aug. 5, 2010

Related U.S. Application Data

(60) Provisional application No. 60/912,072, filed on Apr. 16, 2007.

(51) Int. Cl.
*C12N 1/20* (2006.01)
*C12P 21/06* (2006.01)
(52) U.S. Cl. .................... 435/69.1; 435/252.33
(58) Field of Classification Search .......... None
See application file for complete search history.

(56) References Cited

U.S. PATENT DOCUMENTS 6,083,734 A * 7/2000 Chuang et al. ............. 435/200

FOREIGN PATENT DOCUMENTS

WO   WO 2005/045045   *  5/2005

OTHER PUBLICATIONS

Gershanovitch et al. Repression of inducible Enzyme synnthesis in a mutant of *Eschrichia coli* K 12 deleted for the ptsH gene. !977, Mol. gen. Genet 153, 185-190.*

Ruijter et al. Analysis of mutations that uncoupled transport from phosphorylation in enzyme II(Glc) of *Eschrichis coli* phosphoenolpyruvate-dependent phosphtransferase system.J. Bacteriol. 1992, 174 (9), 2843-2850.*

Chou, Chih-Hsiung et al., Effect of Modified Glucose Uptake Using Genetic Engineering Techniques on High-Level Recombinant Protein Production in *Escherichia coli* Dense Cultures, Biotechnology and Bioengineering (1994) pp. 952-960, vol. 44.

Datsenko, K.A., et al., One-step inactivation of chromosomal genes in *Escherichia coli* K-12 using PCR products, PNAS (2000) pp. 6640-6645, vol. 92, No. 12.

DeAnda, R., et al., Replacement of the glucose phosphotransferase transport system by galactose permease reduces acetate accumulation and improves process performance of *Escherichia coli* for recombinant protein production without impairment of growth rate, Metabolic Engineering 8 (2006) pp. 281-290.

Farmer, W.R., et al., Reduction of Aerobic Acetate Production by *Escherichia coli*, Applied and Environmental Microbiology (1997) pp. 3205-3210, vol. 63, No. 8.

Flores, N., et al., Adaptation for fast growth on glucose by differential expression of central carbon metabolism and *gal* regulon genes in an *Escherichia coli* strain lacking the phosphoenolpyruvate: carbohydrate phosphotransferase system, Metabolic Engineering 7 (2005) pp. 70-87.

Levy, S., et al., Cyclic AMP synthesis in *Escherichia coli* strains bearing known deletions in the *pts* phosphotransferase operon, Elsevier Science Publishers B.V. (1990) pp. 27-33, Gene. 86.

Miller, W.G., et al., An improved GFP cloning cassett designed for prokaryotic transcriptional fusions, Gene 191 (1997) pp. 149-153.

Saffen, D.W., et al., Sugar Transport by the Bacterial Phosphotransferase System, Molecular Cloning and Structural Analysis of the *Escherichia coli ptsH, ptsI*, and *crr* Genes*, The Journal of Biological Chemistry (1987) pp. 16241-16253, vol. 262, No. 33.

Tolentino, G.J., et al., A pH-Regulated Promoter for the Expression of Recombinant Proteins in *Escherichia coli*, Biotechnology Letters (1992) pp. 157-162, vol. 14, No. 3.

Eiteman, M.A., et al., Overcoming acetate in *Escherichia coli* recombinant protein fermentations, Trends in Biology (2006) pp. 530-536, vol. 24, No. 11.

Wagner, A., et al., Sugar Uptake and Carbon Catabolite Repression in *Bacillus* megaterium Strains With Inactivated *ptsHI*, J. Mol. Microbiol. Biotechnol. (2000) 2(4) pp. 587-592.

Baez-Viveros, J.L., et al., Metabolic engineering and protein directed evolution increase the yield of L-phenylalanine synthesized from glucose in *Escherichia coli*. Biotechnol Bioeng 87: 516-524 (2004).

* cited by examiner

*Primary Examiner* — Nashaat Nashed
(74) *Attorney, Agent, or Firm* — Boulware & Valoir (57) ABSTRACT

A method of producing biological products using bacteria with an inactivated ptsHI and wild type err and no added glucose transport activity and which consumes nearly all glucose in the media is described. The ΔptsHI bacteria produce large quantities of recombinant protein without producing significant amounts of acetate. The bacteria grow well on standard LB broth without additional supplementation.

13 Claims, 3 Drawing Sheets

FIG. 1

Figure 1:
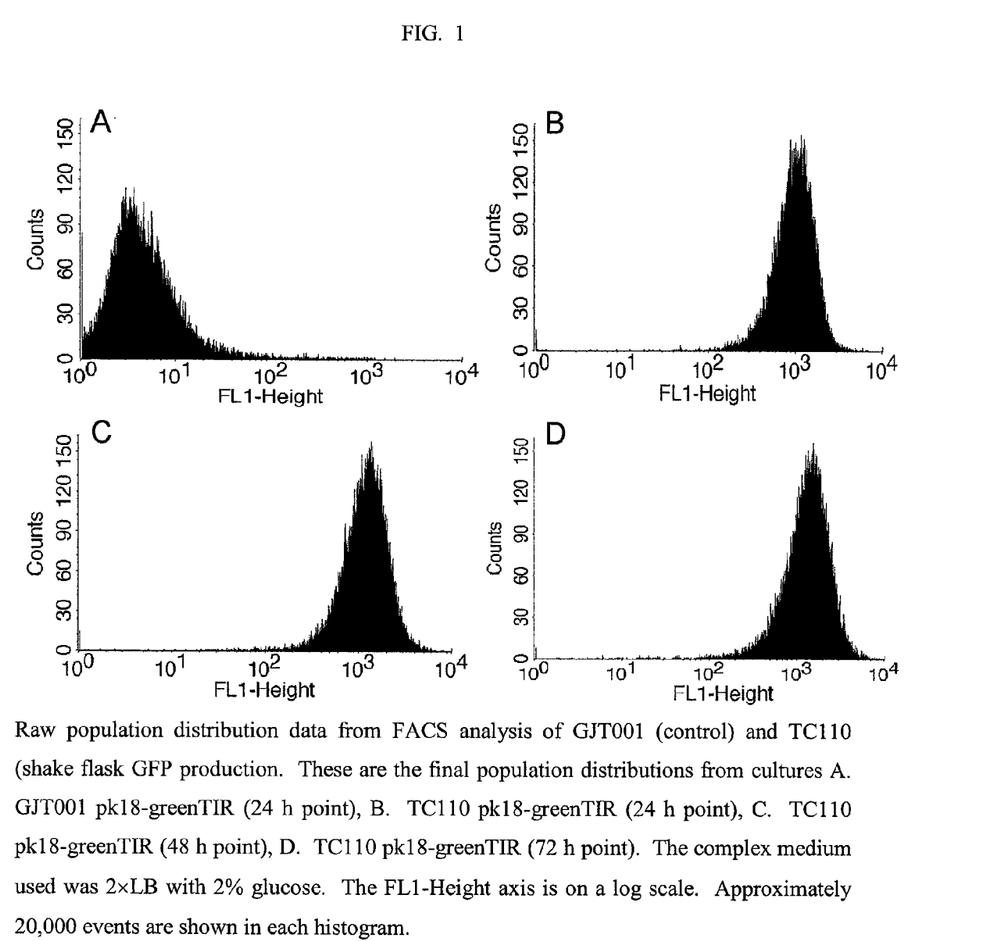
FIG. 1. Single-cell GFP fluorescence assessed in control (GJT001) and mutant (TC110=ΔptsHI ΔlacIYZ) strains at 24, 48 and 72 hours. A. 24 hour GJT001 pk18-greenTOR=control containing GFP. B. 24 hour TC110 pk18-greenTIR=ΔptsHI ΔlacIYZ containing GFP. C. 48 hour TC110 pk18-greenTIR=ΔptsHI ΔlacIYZ containing GFP. D. 72 hour TC110 pk18-greenTIR=ΔptsHI ΔlacIYZ containing GFP. These data show that GFP production is at least two orders of magnitude greater in the mutant than the control (>100 fold).

Raw population distribution data from FACS analysis of GJT001 (control) and TC110 (shake flask GFP production. These are the final population distributions from cultures A. GJT001 pk18-greenTIR (24 h point), B. TC110 pk18-greenTIR (24 h point), C. TC110 pk18-greenTIR (48 h point), D. TC110 pk18-greenTIR (72 h point). The complex medium used was 2×LB with 2% glucose. The FL1-Height axis is on a log scale. Approximately 20,000 events are shown in each histogram.

Figure 2:
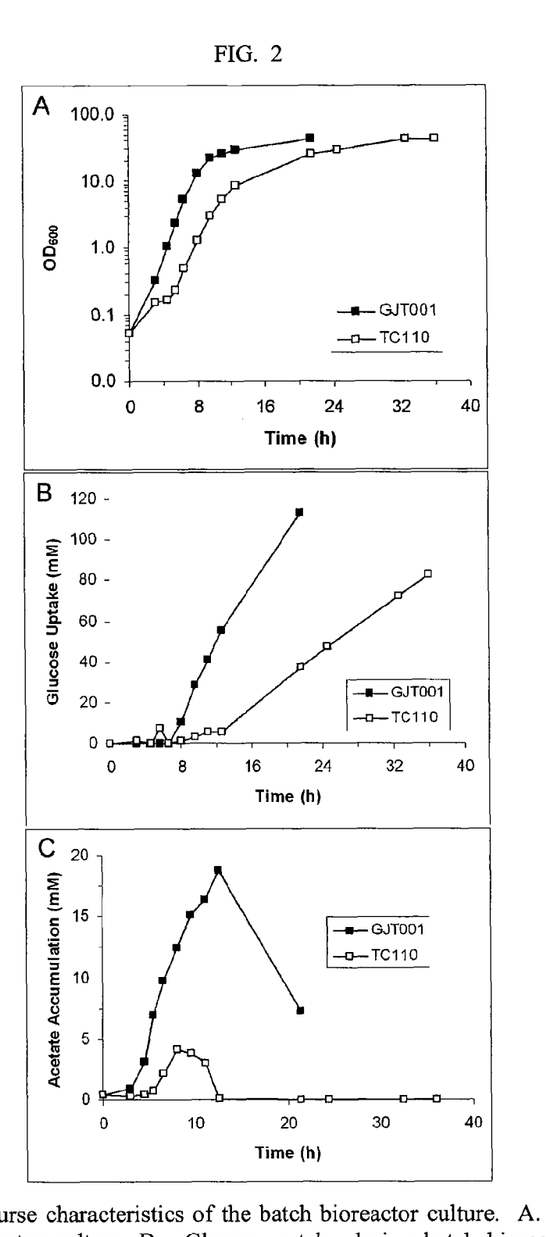
FIG. 2. Time course results for control (GJT001) and ΔptsHI ΔlacIYZ mutant (TC110) growth in a batch bioreactor. A. OD 600 showing growth of the cells. B. Glucose uptake. C. Acetate accumulation.

Figure 2. Time course characteristics of the batch bioreactor culture. A. Growth curves during batch bioreactor culture, B. Glucose uptake during batch bioreactor culture, C. Acetate accumulation during batch bioreactor culture. Graphs show results from one representative experiment.

FIG. 3

Figure 3:
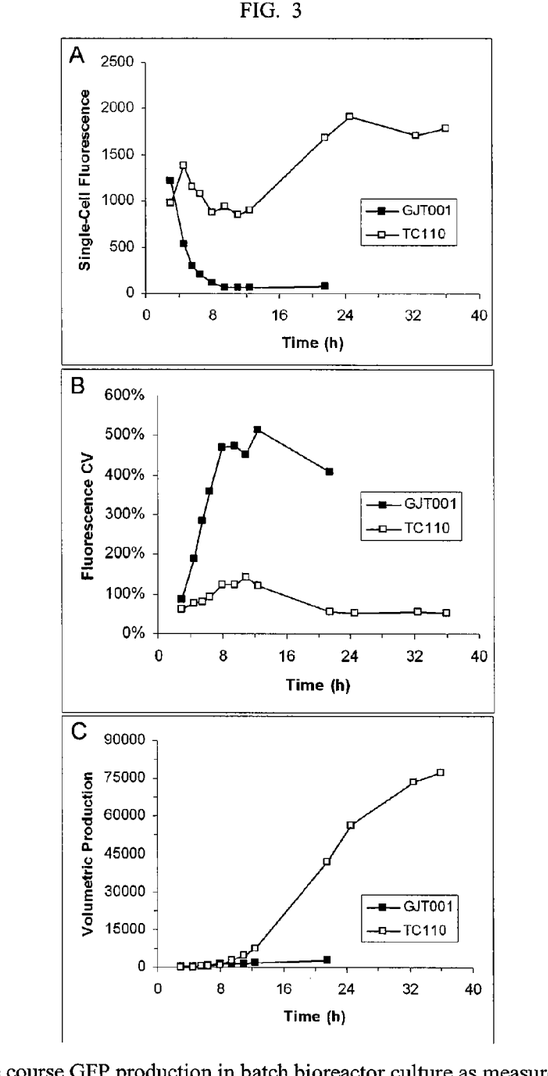
FIG. 3. Time course results of GFP production in batch bioreactor as measured by FACS in control (GJT001) and ΔptsHI ΔlacIYZ mutant (TC110) cells. A. Single cell fluorescence indicating increased GFP production in the ΔptsHI ΔlacIYZ mutant (TC110). B. Coefficient of variation of single cell fluorescence. C. Volumetric production of the culture as determined by single cells fluorescence X OD600 (units of fluorescence X OD/ml).

Figure 3. Time course GFP production in batch bioreactor culture as measured in by FACS. A. Single-cell fluorescence in arbitrary fluorescence units, B. Coefficient of variation of the single-cell fluorescence, C. Volumetric production of the culture. Volumetric production was determined by single-cell fluorescence × $OD_{600}$ (units of fluorescence × OD/ml). Graphs show results from one representative experiment.

REDUCED PHOSPHOTRANSFERASE SYSTEM ACTIVITY IN BACTERIA

CROSS-REFERENCE TO RELATED APPLICATIONS

This application is a 35 U.S.C. Section 371 of PCT/US2008/060383 filed Apr. 15, 2008, which claims priority to U.S. Provisional Application No. 60/ 912,072 filed Apr. 16, 2007, both of which are incorporated herein in their entirety.

FEDERALLY SPONSORED RESEARCH STATEMENT

This invention was made with government support under Grant Number BES-0331324 awarded by the National Science Foundation. The government has certain rights in the invention.

REFERENCE TO MICROFICHE APPENDIX

Not applicable.

FIELD OF THE INVENTION

A novel strain of bacteria with inactivated ptsHI, wild type crr, and with no additional glucose transport added thereto, produces less acetate during fermentation than the wild-type strain. As a result, this strain produces recombinant proteins more efficiently than a wild-type strain. This mutant strain can be used for the production of biological products from a variety of sugar sources.

BACKGROUND OF THE INVENTION

The fermentation of *E. coli* for the commercial production of recombinant proteins has increased significantly in recent years. Although there have been improvements in the productivity of these processes with regard to protein expression, there remains an opportunity for improvement in the fermentation processes. In particular, the production of acetate as a fermentation byproduct is a common problem. Acetate is undesirable because it retards growth even at concentrations as low as 0.5 g/L, and it inhibits protein formation. Moreover, acetate production represents a diversion of carbon that might otherwise have generated biomass or protein product.

In *E. coli*, acetate is synthesized mainly by the phosphotransacetylase-acetate kinase pathway (pta-ackA), using acetyl-CoA as the substrate or from pyruvate by PoxB. Acetate is produced under oxygen-limited culture conditions or during aerobic growth with a high concentration of glucose in the medium. These conditions cause an imbalance between the glycolytic and the TCA cycle fluxes, resulting in the excretion of acetate and other metabolites. There have been a number of attempts to apply metabolic engineering to reduce carbon flow to acetate-producing pathways. However, most of the previous approaches have not completely eliminated acetate production, have a deleterious effect on growth rate, or lead to undesirable pyruvate accumulation.

The main sugar uptake system in many bacteria is the phosphoenolpyruvate sugar phosphotransferase system (PEP-PTS), which mediates the uptake and phosphorylation of carbohydrates. The PEP-PTS is a group translocation process where the transfer of the phosphate moiety of PEP to carbohydrates is catalyzed by the general non-sugar-specific proteins enzyme I and HPr in combination with sugar-specific enzyme II (EII) proteins. After autophosphorylation of enzyme I at the expense of PEP, enzyme I catalyzes the phosphorylation of HPr at histidine 15, resulting in HPr (His-P). The phosphate group from HPr (His-P) is then transferred to the sugar substrate via a two-step phosphorylation reaction mediated by a dedicated EII protein. EII proteins can consist of one or more proteins and are composed of three domains: the EIIA and EIIB domains, which are involved in the phosphotransfer, and the membrane-located EIIC domain, which is most likely involved in the translocation of the sugar substrate. The genes encoding HPr and enzyme I, ptsH and ptsI, respectively, have been cloned from several bacteria and often found to be organized in single operon—ptsHI. Several exemplary genes from a variety of microbes are listed here, and more are available in the public databases:

---

J02796: *E. coli* ptsH, ptsI and crr genes encoding cytoplasmic proteins of the phosphoenolpyruvate:glycose phosphotransferase system (HPr, enzymes I and Glc-III), complete cds AE008764: *Salmonella typhimurium* LT2, section 68 of 220 of the complete genome X12832: *Bacillus subtilis* ptsX, ptsH and ptsI genes for enzyme III-glucose (EC 2.7.1.69), Hpr protein and enzyme I (EC 2.7.3.9) of PEP:sugar phosphtransferase system AY750960: Leuconostoc mesenteroides strain SY1 ptsHI operon, complete sequence; and metal-dependent protease-like protein gene, partial cds Z97203: *Lactococcus lactis cremoris* ptsH and ptsI genes AY064171: *Streptococcus thermophilus* pts operon, complete sequence U12340: *Bacillus stearothermophilus* XL-65-6 phosphoenolpyruvate-dependent phosphotransferase system glucose-specific permease (ptsG') gene, partial cds, HPr (ptsH), enzyme I (ptsI), and PtsT (ptsT) genes, complete cds, and wall associated protein precursor (wapA') gene, complete cds AF291428: *Lactococcus lactis* subsp. *lactis* ptsHI operon, complete sequence AF316496: *Staphylocccus xylosus* ptsHI operon, complete sequence; ubiquinol oxidase (cbdA) gene, partial cds; and unknown genes AF172726: *Lactobacillus sakei* histidyl phosphocarrier protein (ptsI) gene, partial cds; and AtkY (atkY) and copper P-type ATPase AtkB (atkB) genes, complete cds AF159589: *Lactobacillus casei* ptsHI operon, complete sequence; and putative sugar permease gene, complete cds U82366: *Lactobacillus sake* ptsHI operon: histidyl phosphocarrier protein HPr (ptsH) and enzyme I (ptsI) genes, complete cds NC_000913.2: *Escherichia coli* K12

NZ_AAMK01000008.1: *Escherichia coli* 101-1 Ecol1_01_8

NC_007606.1: *Shigella dysenteriae* Sd197

NC_002695.1: *Escherichia coli* O157:H7 str. Sakai

NC_009792.1: *Citrobacter koseri* ATCC BAA-895

NZ_ABEK01000001.1: *Salmonella enterica* subsp. *enterica* serovar *Agona* str. SL483
NC_009436.1: *Enterobacter* sp. 638
NC_009648.1: *Klebsiella pneumoniae* subsp. *pneumoniae* MGH
NC_009832.1: *Serratia proteamaculans* 568
NC_008800.1: *Yersinia enterocolitica* subsp. *enterocolitica* 8081
NC_007712.1: *Sodalis glossinidius* str. 'morsitans'
NC_004547.2: *Erwinia carotovora* subsp. *atroseptica* SCRI1043
NC_008570.1: *Aeromonas hydrophila* subsp. *hydrophila* ATCC 7966
NZ_AAOJ01000004.1: *Vibrio angustum* S14 1099604003201

Expression of *E. coli* ptsHI operon appears to be regulated at the transcriptional level, since mRNA levels were found to be higher in glucose-grown cells than in cells grown on non-PEP-PTS sugars. The PEP-PTS in *E. coli* generates an excess amount of pyruvate during periods of high glucose uptake exceeding the needs of cell growth, which increases carbon flux towards acetate. Previous investigators have reduced acetate accumulation through the deletion of ptsG, which encodes for EIIglc membrane-bound transporter. Others have completely inactivated the PEP-PTS by deleting the entire ptsHIcrr operon (Lévy, 1990), and utilizing GalP (galactose permease) and Glk (glucokinase) activities for glucose uptake (De Anda 2006).

Although De Anda, Flores and associates were able to inactivate the ptsHIcrr operon, the mutant ΔptsHIcrr bacteria did not grow rapidly and protein production was reduced due to poor bacterial growth and increased acetate production (Flores, 2005a; Flores, 2005b; De Anda, 2006). Acetate production was increased due to the additional GalP and Glk mutations that allowed glucose transport and phosphorylation. Additionally, these bacteria required minimal media to reduce acetate production, further slowing bacterial growth and biomass accumulation.

Therefore, a method of improving ΔptsHI bacterial growth while maintaining low acetate production and PEP required for bio-production is still required.

SUMMARY OF THE INVENTION

The invention relates to bacteria having an inactivated ptsHI with wild type crr and no added glucose transport genes or activity. In this environment, acetate production is reduced to almost zero, and recombinant protein production is increased more than 25 fold and under some conditions more than 100 fold. Yet, the bacteria can still grow on standard LB medium, and can use a wide variety of sugars as a carbon source. The genes and proteins discussed herein are identified below:

TABLE 1

| GENE | PROTEIN |
| --- | --- |
| crr | PEP-PTS enzyme IIIGlc IIGlcA |
| ptsI | PEP-PTS enzyme I |
| ptsH | PEP-PTS enzyme HPr |
| ptsG | PEP-PTS enzyme IIGlc (CB) |

PEP-PTS = phosphoenolpyruvate phosphotransferase system

The invention also generally relates to a method of producing recombinant protein by culturing a bacteria under conditions to express a recombinant protein, and isolating said recombinant protein. The bacteria has wild type crr, inactivated ptsHI and adequate wild type glucose transport. These bacteria accumulate essentially no acetate during growth, and produce large amounts of recombinant protein, over 100 fold more recombinant protein than the same strain without inactivated ptsHI in flasks and over 25 more in batch culture. The bacteria can be *Escherichia, Salmonella, Bacillus, Leuconostoc, Lactococcus, Streptococcus, Pseudomonas, Staphyloccus, Shigella, Citrobacter, Enterobacter, Klebsiella, Serratia, Yersinia, Sodalis, Erwinia, Aeromonas* and *Vibrio* species, but preferably is *Escherichia coli*.

DESCRIPTION OF THE DRAWINGS

GFP production is measured as an example of recombinant protein production in the strains of the invention in the following figures. However, the use of GFP is exemplary only, and should not be construed as limiting. Any recombinant protein can be used in the invention.

DESCRIPTION OF EMBODIMENTS OF THE INVENTION

| Abbr | Term |
| --- | --- |
| μ | growth rate |
| Ap/Ap$^R$ | ampicillin/ampicillin resistance |
| ATCC ® | AMERICAN TISSUE-TYPE CULTURE COLLECTION ™ |
| Cm | chloramphenicol |
| Cn | carbenicillin |
| ColE1 | gram-negative origin of replication |
| Em | erythromycin |
| FAD | flavin adenine dinucleotide |
| FMN | flavin mononucleotide |
| FRD | fumarate reductase |
| GC-MS | gas chromatography-mass spectroscopy |

-continued

| Abbr | Term |
|---|---|
| GFP | green fluorescent protein |
| Km/Km$^R$ | kanamycin/kanamycin resistance |
| MLS$^R$ | macrolide, lincosamide and streptogramin A resistance |
| Nal | nalidixic acid |
| NCBI™ | NATIONAL CENTER FOR BIOTECHNOLOGY INFORMATION ™ |
| Orill | gram-positive origin of replication |
| Ox/Ox$^R$ | oxacillin/oxacillin resistance |
| Sm/Sm$^R$ | streptomycin/streptomycin resistance |
| Tc | tetracycline |
| Thi$^R$/Cm$^R$ | thiamphenicol/chloramphenicol resistance |
| wt | wild-type |

A culture that accumulates "essentially no acetate" produces ≦10%, preferably ≦2%, and most preferably ≦1% of the acetate produced in a batch-fed culture by cells without a ΔptsHI mutation, wherein the acetate is measured by HPLC at entry to stationary phase. In one embodiment, a culture that accumulates "essentially no acetate" is a ΔptsHI cell strain that produces ≦10 mM acetate when grown under batch-fed conditions with 2×LB+2% glucose. In another embodiment, a culture that accumulates "essentially no acetate" is a ΔptsHI cell strain that produces less than 7.5 mM acetate in CSL medium with 2% glucose at 24 hrs, and no detectable acetate at 48 hrs.

By lacking "recombinant or added glucose transport systems" what is meant is that the endogenous glucose transport genes are not recombinantly overexpressed, nor are additional glucose transport systems, such as glf, GalP or GLK, added thereto.

Although, we do not add any extra glucose transport systems, the overall glucose uptake of the culture is slower due to the ΔptsHI mutation. It is possible, however, to get as high as 100% glucose uptake from the media, as the native non-ptsHI systems compensate for the ΔptsHI mutant or if we allow for longer growth periods.

As used herein "recombinant" is relating to, derived from, or containing genetically engineered material. Recombinant DNA is DNA produced by artificially joining molecules derived from various biological sources.

"Recombinant protein" as used herein refers to any protein expressed from genetically engineered coding sequences operably linked with an active or inducible promoter for expression of the protein product. Many recombinant proteins are routinely and commercially prepared using bacterial expression systems known to one of ordinary skill in the art. The invention is designed to increase production of any recombinant protein in bacterial cells and should not be limited to the exemplified GFP, which is merely an easily measured exemplary reporter protein.

The terms "operably associated" or "operably linked," as used herein, refer to functionally coupled nucleic acid sequences.

"Reduced activity" is defined herein to be at least a 75% reduction in protein activity, as compared with an appropriate control species. Preferably, at least 80, 85, 90, or 95% reduction in activity is attained, and in the most preferred embodiment, the activity is eliminated or "inactivated" (~100% or insignificant detectable activity). Proteins can be inactivated with inhibitors, by mutation, or by suppression of expression or translation, and the like. By "null mutant" or "null mutation" what is meant is that protein activity is completely eliminated. In one example, the gene of interest is completely removed by homologous recombination with a plasmid containing a null mutant. Null mutants can be created by mutation, deletion, truncation, addition of stop codons, and the like.

"Overexpression" or "overexpressed" is defined herein to be greater than 125% of wild type activity.

The terms "disruption" and "disruption strains," as used herein, refer to cell strains in which the native gene or promoter is mutated, deleted, interrupted, or down-regulated in such a way as to decrease the activity of the gene. A gene is completely (100%) reduced by knockout or removal of the entire genomic DNA sequence. Use of a frame shift mutation, early stop codon, point mutations of critical residues, or deletions or insertions, and the like, can completely inactivate (100%) gene product by completely preventing transcription and/or translation of active protein.

The term "exogenous" indicates that the protein or nucleic acid is a non-native molecule introduced from outside the organism or system without regard to species of origin. For example, an exogenous peptide may be applied to the cell culture; an exogenous RNA may be expressed from a recombinant DNA transfected into a cell; or a native gene may be under the control of exogenous regulatory sequences.

A gene or cDNA may be "optimized" for expression in *E. coli* or other bacterial species using the codon bias for the species. NCBI™ provides codon usage databases for optimizing DNA sequences for protein expression in various species.

In calculating "% identity" the unaligned terminal portions of the query sequence are not included in the calculation. The identity is calculated over the entire length of the reference sequence; thus short local alignments with a query sequence are not relevant (e.g., % identity=number of aligned residues in the query sequence/length of reference sequence). Alignments are performed using BLAST homology alignment as described by Tatusova T A & Madden T L (1999) FEMS Microbiol. Lett. 174:247-50. The default parameters were used, except the filters were turned OFF. As of Jan. 1, 2001 the default parameters were as follows: BLASTN or BLASTP as appropriate; Matrix=none for BLASTN, BLOSUM62 for BLASTP; G Cost to open gap default=5 for nucleotides, 11 for proteins; E Cost to extend gap [Integer] default=2 for nucleotides, 1 for proteins; q Penalty for nucleotide mismatch [Integer] default=−3; r reward for nucleotide match [Integer] default=1; e expect value [Real] default=10; W word size [Integer] default=11 for nucleotides, 3 for proteins; y Dropoff (X) for blast extensions in bits (default if zero) default=20 for blastn, 7 for other programs; X dropoff value for gapped alignment (in bits) 30 for blastn, 15 for other programs; Z final X dropoff value for gapped alignment (in bits) 50 for blastn, 25 for other programs.

This program is available online at NCBI™ (ncbi.nlm.nih.gov/BLAST/).

The terms "about" and "approximately" may be used herein to mean within 2 standard deviations, more preferably within 1 standard deviation, or even 0.5 standard deviations depending upon the system and statistical analysis used. "About" and "approximately" may also be used herein to mean within 10%, more preferably within 5%, and most preferably within 1% of the reported value.

The invention is exemplified with *E. coli*, but that is for convenience and simplicity only and other well known bacteria can be modified in the same way, especially where (as here) the genes of interest are well known and the same cloning techniques are applicable to many species. Thus, the invention can also be applied to other *Escherichia* species, as well as *Salmonella, Bacillus, Leuconostoc, Lactococcus, Streptococcus, Pseudomonas, Staphylocccus, Shigella, Cit-* robacter, Enterobacter Klebsiella, Serratia, Yersinia, Sodalis, Erwinia, Aeromonas* and *Vibrio* species, each of which has already identified ptsHI genes that can easily be disrupted. However, the most commercially useful species are the *Escherichia*, especially *E. coli* and it is preferred.

The phosphoenolpyruvate phosphotransferase system (PEP-PTS) is a protein complex consisting of PEP-PTS enzyme I, PEP-PTS enzyme HPr, and one or more PEP-PTS enzyme II proteins. PEP-PTS enzyme I (ptsI) and PEP-PTS enzyme HPr (ptsH) can be found in a single operon (ptsHI) or separately, depending upon the bacterial strain and genomic organization. In some instances the ptsHI operon may be removed and the crr gene left intact, alternatively, if the crr gene is also removed, it may be re-inserted on a plasmid or at a unique location in the genome. In one embodiment, the ptsHI operon is replaced with an intact and functional crr gene. In another embodiment just ptsHI are knocked out and crr is left intact.

Herein, ΔptsHI is defined as a bacterial strain with the ptsH and/or ptsI genes inactivated. The ptsH and ptsI genes may be inactivated individually or the entire ptsHI operon may be inactivated at once. Further, individual mutations alone will suffice to eliminate the activity of the protein complex.

The PEP-PTS enzyme HPr (ptsH) is currently found in over 500 bacterial species. The reference sequence for *E. coli* can be found at GENBANK™ accession number NP_416910. HPr proteins range continuously from 100% identity in *E. coli* to about 40% identity in *Pseudomonas aeruginosa*. HPr proteins are members of the PEP-PTS HPr family defined by the conserved Histidine-containing phosphocarrier protein activity. All members of this family catalyze the phosphorylation of sugar substrates during their translocation across the cell membrane.

The PEP-PTS enzyme I (ptsI) is found in over 1000 bacterial species. The reference sequence for *E. coli* can be found at GENBANK™ accession number NP_416911. PEP-PTS EI proteins range continuously from 100% identity in *E. coli* to about 40% identity in Magnetospirillum. PEP-PTS EI proteins are members of the phosphoenolpyruvate-protein kinase family. All members of this family are PEP utilizing enzymes that catalyze the phosphorylation of HPr.

The *E. coli* ptsHI operon is found at GenBank accession number J02796, and is also present in over 400 bacteria. PtsHI operons have been identified with 100% identity in *E. coli*. Other ptsHI operons like those in *Yersinia* have segments of 80% identity in portions of the ptsHI genes, but much less overall identity.

The lacIYZ operon encodes the lac repressor, lactose permease and beta-galactosidase, respectively. It was deleted herein for research on another project, but these genes are incidental and have no effect on the invention.

Common restriction enzymes and restriction sites are found at NEB® (NEW ENGLAND BIOLABS®, neb.com) and INVITROGEN® (invitrogen.com). ATCC®, AMERICAN TYPE CULTURE COLLECTION™ (atcc.org) has an extensive collection of cell strains that are publicly available and incorporated herein by reference.

Example 1

Mutant Production and Growth

TABLE 2

| Strains and Plasmids | | |
|---|---|---|
| | Characteristics | Source |
| Strains | | |
| GJT001 | Control: Spontaneous cadR mutant of MC4100 (ATCC35395) Δlac(arg-lac)U169rpsL150relA1 ptsF SmR | Tolentino, 1992 |
| TC110 | GJT001 ΔptsHI | This study |
| Plasmids | | |
| pCR2.1-TOPO | ApR, KmR, Plac, pUC ori, f1 ori | Invitrogen |
| p10044 | glf from *Zymamonas mobilis* in pCR2.1-TOPO | This study |
| pk18-greenTIR | gfp from *Aequorea victoria* in pk18 | Miller & Lindow, 1997 |
| pk18-lacZ | lacZ from *Escherichia coli* in pk18 | This study |

The strains and plasmids used in this study are listed in Table 2. The mutant ΔptsHI strain (TC110) was constructed using the Datsenko and Wanner method (Datsenko and Wanner, 2000). The mutations were done sequentially: ptsHI was deleted from GJT001, and lacIYZ was deleted from GJT001 ΔptsHI. In short, a linear DNA was constructed using PCR. The sequences of primers for ptsHI are not shown. The linear DNA contained bases that were homologous to the upstream region of the gene of interest, the kanamycin (Km) resistance gene that was flanked with FRT sites, and bases that were homologous to the other end of the gene of interest (exact bases are not shown). The linear DNA was transferred into the *E. coli* strain GJT001 carrying a lambda red expression plasmid and colonies containing the homologous recombination were selected using Km resistance. After selection, the Km resistance gene was eliminated by introducing a temperature-sensitive plasmid that expressed the FLP recombinase, which excised the Km cassettes bounded by FRT sites. The mutation was then verified using PCR verification with appropriate primers. A phenotype test (severely reduced growth rate and glucose uptake rate in glucose-supplemented M9 Minimal medium) was also used to verify the ptsHI deletion. Using this method, the strains GJT001 ΔptsHI, Km$^R$, GJT001 ΔptsHI, GJT001 ΔptsHI, Km$^R$, and GJT001 ΔptsHI were constructed. The mutant strain GJT001 ΔptsHI was designated TC110, and is referred to herein as either TC110 or as ΔptsHI.

The standard formulations of LB broth (10 g/L tryptone, 5 g/L yeast extract, 10 g/L NaCl) and M9 minimal medium were used. The 2×LB medium contained 20 g/L tryptone, 10 g/L yeast extract, and 10 g/L NaCl. The corn steep liquor (CSL) medium contained 33.3 g/L corn steep liquor, 1.4 g/L $K_2HPO_4$, 0.6 g/L $KH_2PO_4$, 3.3 g/L $(NH_4)_2SO_4$, and 0.2 g/L $MgSO_4$. Strains were grown in shaker flasks or in batch bioreactors, as indicated. GFP production was measured by FACS or fluorometer periodically. Metabolites were measured by HPLC.

Example 2

Acetate Eliminated

Once the needed control (GJT001) and ΔptsHI (TC110) cells were made, we measured cell growth by increase in optical density and glucose consumption, and also measured acetate production.

TABLE 3

Growth and metabolite data from shake flask GFP production study

| Strain | Medium & % Glucose | Incubation (h) | OD600 | Glucose Consumed (mM) | Acetate Accumulated (mM) |
|---|---|---|---|---|---|
| GJT001 | LB + 1% | 24 | 6.6 ± 0.1 | 36.9 ± 0.3 | 55.5 ± 1.6 |
| | LB + 2% | 24 | 6.8 ± 0.2 | 44.7 ± 1.3 | 73.4 ± 0.9 |
| | 2 × LB + 2% | 24 | 8.0 ± 0.2 | 46.8 ± 0.8 | 90.4 ± 1.6 |
| TC110 | LB + 1% | 24 | 13.8 ± 0.6* | 26.4 ± 0.6 | 0.0 ± 0.0* |
| | | 48 | 18.8 ± 0.2* | 58.5 ± 0.1* | 0.0 ± 0.0* |

TABLE 3-continued

Growth and metabolite data from shake flask GFP production study

| Strain | Medium & % Glucose | Incubation (h) | OD600 | Glucose Consumed (mM) | Acetate Accumulated (mM) |
|---|---|---|---|---|---|
| | LB + 2% | 24 | 13.0 ± 0.7* | 29.9 ± 1.7 | 0.0 ± 0.0* |
| | | 48 | 19.0 ± 0.7* | 87.9 ± 3.4* | 1.3 ± 1.9* |
| | 2 × LB + 2% | 24 | 14.8 ± 0.4* | 27.0 ± 1.6 | 0.1 ± 0.2* |
| | | 48 | 18.8 ± 0.8* | 64.6 ± 5.2* | 0.0 ± 0.0* |
| | | 72 | 23.5 ± 0.7* | 116.1 ± 0.5* | 9.1 ± 6.6* |

Fermentations were conducted at 32° C. 1% glucose~56 mM and 2% glucose~112 mM. Medium indicates the type of medium used and the starting glucose content. $OD_{600}$ is the final optical density of the culture. Glucose Consumed shows the reduction in glucose concentration at the end of the incubation. Acetate Accumulated shows the acetate accumulated at the end of the incubation. Data points shown are averages of quadruplicates (n=4) with standard deviations. * indicates that the data are significantly different from the control data for the corresponding strain and medium composition, P<0.05.

Although the total glucose consumed at 48 hrs in both the wild-type GJT001 cells and ΔptsHI TC110 cells approaches the same level of glucose consumption, the overall rate of glucose consumption is reduced in the ΔptsHI cells. Note in Table 3 that at 24 hrs, the wild-type cells have consumed 36.9 mM, 44.7 mM and 46.8 mM glucose dependent upon the glucose and LB concentration. At 24 hrs, the ΔptsHI cells have only consumed 26.4 mM, 29.9 mM, 27.0 mM glucose under the same conditions. Thus the ΔptsHI cells have consumed only 72%, 67% and 58% of the glucose consumed by wild-type cells after 24 hours, respectively.

The data clearly shows that ΔptsHI reduces acetate production to almost zero, and in all cases to less than 10 mM. Yet the cells continue to grow as indicated by increased optical density and glucose consumption.

Example 3

Protein Increased

Once we confirmed that acetate was greatly reduced in the ΔptsHI mutant, we then measured the production of a reporter protein, in this case green fluorescent protein (GFP), in control GFP producing cells (GJT001 pk18-greenTIR) and ΔptsHI GFP producing cells (TC110 pk18-greenTIR).

TABLE 4

Flow cytometry data from shake flask GFP production study

| Strain | Medium & % glucose | Incubation (h) | Single-Cell Fluorescence | Fluorescence CV | Volumetric Productivity |
|---|---|---|---|---|---|
| GJT001 pk18-greenTIR | LB + 1% | 24 | 10.9 ± 0.5 | 402% ± 34% | 71.2 ± 3.1 |
| | LB + 2% | 24 | 10.2 ± 1.3 | 673% ± 21% | 69.7 ± 9.2 |
| | 2 × LB + 2% | 24 | 10.6 ± 1.3 | 467% ± 35% | 84.3 ± 10.5 |
| TC110 pk18-greenTIR | LB + 1% | 24 | 730 ± 17* | 47% ± 1%* | 10089 ± 470* |
| | | 48 | 729 ± 21* | 47% ± 0%* | 13732 ± 430* |
| | LB + 2% | 24 | 900 ± 4* | 63% ± 1%* | 11727 ± 630* |
| | | 48 | 1017 ± 32* | 64% ± 1%* | 19276 ± 930* |
| | 2 × LB + 2% | 24 | 1056 ± 4* | 49% ± 2%* | 15575 ± 470* |
| | | 48 | 1337 ± 50* | 52% ± 1%* | 25082 ± 1400* |
| | | 72 | 1392 ± 41* | 55% ± 1%* | 32728 ± 1400* |

Fermentations were conducted at 32° C. 1% glucose~56 mM and 2% glucose~112 mM. Medium indicates the type of medium used and the starting glucose content. Single-Cell Fluorescence is measured in arbitrary fluorescence units. Fluorescence CV is the coefficient of variation of the single-cell fluorescence across the cell population. Volumetric Productivity is the product of the Single-Cell Fluorescence and the $OD_{600}$ for each condition. The units are in terms of arbitrary fluorescence×OD/ml. Data points shown are averages of quadruplicates (n=4) with standard deviations. * indicates that the data are significantly different from the control data for the corresponding strain and medium composition, P<0.05.

The data shows a very large increase in GFP produced. Additionally, the variability in GFP producing cells was greatly diminished. There are two likely reasons for the mutant's increase in productivity. First, the glucose uptake rate was sufficiently low to avoid triggering acetate excretion, which prevented the inhibition of cell growth and recombinant protein synthesis. Despite the mutant's lower specific growth rate in the early exponential phase, the mutant reached equal or greater cell densities due to the lack of inhibition by acetate accumulation. Second, the lack of acetate accumulation allowed the cultures to produce recombinant protein for a longer period of time, further increasing the volumetric productivity.

The rate of recombinant protein production is an important issue in industry. While our mutant strain performed well, it took 72 h to reach its final volumetric productivity in shake flasks, which was triple the time needed for the wild-type. The 25% reduction in specific growth rate indicated that the glucose uptake rate was too slow to maintain optimal growth. The situation was improved in the batch bioreactors, where TC110 finished its run in 36 h versus 21.5 h for GJT001. Given the amount of extra GFP produced, the increased incubation time was well justified.

Example 4

Other Media

We also tested whether the greatly increased production could be attained in other media. Therefore, we tested control GFP producing cells (GJT001 pk18-greenTIR) and ΔptsHI GFP producing cells (TC110 pk18-greenTIR) in CSL media (see above for recipe).

TABLE 5

Shake flask GFP production in CSL medium.

| Strain | Incubation (h) | OD600 | Volumetric Productivity (Fluorescence) | Glucose Consumed (mM) | Acetate Accumulated (mM) |
|---|---|---|---|---|---|
| GJT001 pk18-greenTIR | 24 | 9.7 ± 0.1 | 10.8 ± 0.5 | 31.1 ± 1.6 | 29.6 ± 0.7 |
| TC110 pk18-greenTIR | 24 | 10.5 ± 0.6 | 143.3 ± 13* | 31.4 ± 2.3 | 7.2 ± 1.9* |
|  | 48 | 17.0 ± 0.3* | 307.7 ± 21* | 51.3 ± 1.8* | 0.0 ± 0.0* |

Fermentations were conducted at 32° C. in CSL medium with 2% glucose (~112 mM). OD600 is the final optical density of the culture. Volumetric Productivity is the fluorescence of a fixed volume of fermentation broth, measured in arbitrary units of fluorescence/ml. Glucose Consumed shows the reduction in glucose concentration at the end of the incubation. Acetate Accumulated shows the acetate accumulated at the end of the incubation. Data points shown are averages of triplicates (n=3) with standard deviations. * indicates that the data are significantly different from the control data for the corresponding strain and medium composition, P<0.05.

Again, acetate production is greatly reduced and GFP production increased, even in the CSL media.

Example 5

Other Proteins

We also tested another recombinant protein β-galactosidase (data not shown) to ensure that the greatly improved results were universal, and not just an effect seen with GFP. Acetate was reduced to zero by 72 hours, but volumetric protein increase over control was not as high for β-galactosidase (7.5 fold increase over control) as with GFP. The relatively small performance gain is because the wild-type already produces a significant amount of β-galactosidase. Using previous data, we estimate that the wild-type expression of β-galactosidase protein may account for up to 6.7% of total cellular protein, which is quite significant. By comparison, the wild-type strain expressed very low levels of GFP that could easily be increased. Mutant expression of β-galactosidase protein accounted for 19.8% of total cellular protein, which is significant production of recombinant protein and in addition a higher cell density was attained. Therefore, although the ratio of total β-galactosidase protein mutant/ control was not as high, recombinant protein production was still extremely good, confirming that the invention has broad applicability to any recombinant protein.

Example 6

Added Glucose Transport

We know from previous experiments that ΔptsHI in combination with overexpressed galP and native glk activities had growth rates similar to control cells, but had significant acetate accumulation and decreased production of recombinant protein (De Anda 2006). We tested whether this was a general phenomena by adding glucose transport to the ΔptsHI GFP producing strain. We used glf from *Zymomonas mobilis* in pCR2.1-TOPO and pCR2.1-TOPO alone to test production of GFP in a GFP producing ΔptsHI strain (data not shown). As in previous work, the addition of glucose transport resulted in greatly increased acetate accumulation with deleterious effects on cell growth and accumulation of recombinant protein. Therefore, it is important not to overexpress or add exogenous glucose transport to obtain the significant improvements in recombinant protein yield.

Example 7

Deleted CRR

Lévy et al., made a strain similar to that described herein, but also having a deletion in crr gene (encoding enzyme IIIGlc (IIGlcA) of the PEP-PTS). In the Lévy article, the growth characteristics of a ΔptsHI-crr mutant strain on MacConkey agar plates supplemented with various carbon sources indicated that the mutants could not metabolize maltose, melbiose, sorbitol, or rhamose. For our strain, colonies formed on MacConkey agar plates supplemented with glucose, mannose, sorbitol, glycerol, maltose and rhamnose all turned red, indicting that our ΔptsHI strain behaves very similar to that of the wild type. Therefore, for full complement of usable carbon resources, it is important that the strain have wild type crr.

Example 8

Batch Reactor Growth

Our mutant strain almost completely eliminated acetate accumulation, which allowed the mutant to grow more efficiently and for a longer period of time. In shake flask cultures, ΔptsHI generally achieved a 50% increase in OD600 as compared with control after an equal incubation time. Eventually, the final OD600 was approximately 3-fold higher. We then tested growth in a batch reactor to determine if the results could be scaled up. The results are shown in FIG. 1-3.

FIG. 1 shows that the ΔptsHI has more than 100 fold more GFP than the control at all time points. FIG. 2 confirms that growth (FIG. 2A) and glucose consumption (FIG. 2B) are reduced in the ΔptsHI mutant as compared with control, and that acetate accumulation (FIG. 2C) is almost undetectable. FIG. 3 shows a time course of GFP production (FIG. 3A), decreased variability (FIG. 3B), and increased volumetric production (FIG. 3C).

In the batch bioreactor, the results when expressed as a ratio of mutant over control were markedly different due to the significantly improved performance of the control (GJT001 pk 18-greenTIR). At an equal incubation time, ΔptsHI (TC110 pk 18-greenTIR) had approximately 60% of the $OD_{600}$ achieved by control. ΔptsHI's final $OD_{600}$ was equal to that of control, but was achieved 15 h later. The control cells improved performance was due to the improved aeration of the bioreactor versus the flasks and the pH control afforded by the bioreactor setup. Even so, there is significant production of recombinant protein in the ΔptsHI strain and the final volumetric productivity of TC110 was 25-fold higher over the final volumetric productivity of the corresponding GJT001 culture.

TC110 did not require pH control during its bioreactor culture due to its lack of acetate accumulation. The lack of acetate accumulation eliminates the need to add counter ions during the acetate formation and re-absorption stages to control pH. The benefit will be that the final broth will contain fewer ions, which will lower the purification cost of some processes.

In conclusion, TC100 was constructed by deleting ptsHI to reduce the glucose uptake rate. The specific growth rate of the mutant was reduced by approximately 25% in complex medium for growth both in shake flasks and batch bioreactors. The mutant achieved about a 90% reduction or more in acetate accumulation and completely eliminated acetate accumulation under most conditions. The reduction in acetate accumulation and increase in cell density were responsible for the 7.5-fold and 385-fold increases in final volumetric productivity for β-galactosidase and GFP, respectively, in shake flask cultures. The final volumetric productivity increase for GFP was 25-fold in batch bioreactor cultures. These results confirm previous findings that modification of glucose uptake is an effective approach to improving performance in complex media. Other factors limiting the culture performance can be explored, and together, these strategies can further increase culture productivity for recombinant protein production.

REFERENCES

All references are listed herein for the convenience of the reader. Each is incorporated by reference in its entirety.

1. Chou, et al., "Effect of Modified Glucose-Uptake Using Genetic-Engineering Techniques on High-Level Recombinant Protein-Production in *Escherichia-Coli* Dense Cultures." Biotech. Bioeng. 44:952-60 (1994).
2. Datsenko and Wanner "One-step inactivation of chromosomal genes in *Escherichia coli* K-12 using PCR products." Proc Natl Acad Sci USA. 97:6640-5 (2000).
3. De Anda, et al., "Replacement of the glucose phosphotransferase transport system by galactose permease reduces acetate accumulation and improves process performance of *Escherichia coli* for recombinant protein production without impairment of growth rate." Metab Eng 8:281-90 (2006).
4. Farmer and Liao, "Reduction of aerobic acetate production by *Escherichia coli*." Appl. Env. Microbio. 63:3205-10 (1997).
5. Flores, et al., "Role of pyruvate oxidase in *Escherichia coli* strains lacking the phosphoenolpyruvate:carbohydrate phosphotransferase system." J Mol Microbiol Biotechnol. 8:209-21 (2004).
6. Flores, et al., "Nutrient-scavenging stress response in an *Escherichia coli* strain lacking the phosphoenolpyruvate: carbohydrate phosphotransferase system, as explored by gene expression profile analysis." J. Mol. Microbiol. Biotechnol. 10:51-63 (2005).
7. Flores, et al., "Adaptation for fast growth on glucose by differential expression of central carbon metabolism and gal regulon genes in an *Escherichia coli* strain lacking the phosphoenolpyruvate:carbohydrate phosphotransferase system." Metab Eng. 7:70-87 (2005).
8. Lévy S, et al., Cyclic AMP synthesis in *Escherichia coli* strains bearing known deletions in the pts phosphotransferase operon. 86:27-33 (1990).
9. Miller, W. G.; Lindow, S. E., An improved GFP cloning cassette designed for prokaryotic transcriptional fusions. Gene 191:149-53 (1997).
10. Saffen, et al., "Sugar transport by the bacterial phosphotransferase system. Molecular cloning and structural analysis of the *Escherichia coli* ptsH, ptsI, and crr genes." J. Biol. Chem. 262:16241-53 (1987).
11. San, et al., "Strategies in High-Level Expression of Recombinant Protein in *Escherichia-Coli*." Recombinant DNA Technology II, 721:257-67 (1994).
12. Tolentino, et al., "A Ph-Regulated Promoter for the Expression of Recombinant Proteins in *Escherichia Coli*." Biotech. Let. 14:157-62 (1992).

What is claimed is:

1. A method of producing recombinant protein comprising:
   a) culturing an *Escherichia coli* bacteria under conditions to express a recombinant protein, and
   b) isolating said recombinant protein,
   wherein said bacteria has i) wild type crr (phosphoenolpyruvate sugar phosphotransferase system enzyme IIIGlc/IIGlcA); ii) inactivated ptsHI (phosphoenolpyruvate sugar phosphotransferase system enzyme I-enzyme HPr) and iii) no recombinant glucose transport activity added thereto, and wherein said bacteria accumulate less than 7.5 mm acetate during aerobic growth for at least 24 hours at 32° C. in a medium comprising 2% glucose.

2. The method of claim 1, wherein said bacteria produces more than 7.5 fold more recombinant protein than the same strain without inactivated ptsHI.

3. The method of claim 1, wherein said bacteria produces more than 25 fold more recombinant protein than the same strain without inactivated ptsHI.

4. The method of claim 1, wherein said bacteria produces more than 100 fold more recombinant protein than the same strain without inactivated ptsHI.

5. The method of claim 1, wherein said bacteria comprise a deletion of ptsH or ptsI or both.

6. The method of claim 1, wherein said culture comprises LB broth with 10 g/L tryptone, 5 g/L yeast extract, 10 g/L NaCl.

7. The method of claim 1, wherein said bacteria consume greater than 90% of the glucose present in the culture.

8. The method of claim 1, wherein said the total amount of acetate accumulated is less than 7 mM.

9. The method of claim 1, wherein said the total amount of acetate accumulated is less than 5 mM.

10. The method of claim 1, wherein said the total amount of acetate accumulated is less than 3 mM.

11. The method of claim 1, wherein said the total amount of acetate accumulated is less than 1 mM.

12. A recombinant bacteria having wild type non-PEP-PTS glucose transport activity, wild type crr and ΔptsHI.

13. A method of producing recombinant protein comprising:
   a) culturing a bacteria under conditions to express a recombinant protein, and
   b) isolating said recombinant protein,
   wherein said bacteria is *Escherichia coli* and has wild type crr, ΔptsHI and no added recombinant glucose transport activity, and wherein said bacteria accumulate less than 10 mM acetate during aerobic growth for at least 24 hours at 32° C. in a medium comprising 2% glucose and produces more than 25 fold more recombinant protein than the same strain without ΔptsHI.

* * * * *

UNITED STATES PATENT AND TRADEMARK OFFICE
CERTIFICATE OF CORRECTION

PATENT NO.        : 8,236,525 B2
APPLICATION NO.   : 12/596399
DATED             : August 7, 2012
INVENTOR(S)       : Ka-Yiu San et al.

Page 1 of 1

It is certified that error appears in the above-identified patent and that said Letters Patent is hereby corrected as shown below:

In column 14, line 64, the word "said" should be deleted such that Claim 8 reads as "The method of claim 1, wherein the total amount of acetate accumulated is less than 7 mM."

In column 14, line 66, the word "said" should be deleted such that Claim 9 reads as "The method of claim 1, wherein the total amount of acetate accumulated is less than 5 mM."

In column 15, line 1, the word "said" should be deleted such that Claim 10 reads as "The method of claim 1, wherein the total amount of acetate accumulated is less than 3 mM."

In column 15, line 3, the word "said" should be deleted such that Claim 11 reads as "The method of claim 1, wherein the total amount of acetate accumulated is less than 1 mM."

Signed and Sealed this
Twenty-third Day of October, 2012

David J. Kappos
*Director of the United States Patent and Trademark Office*